United States Patent [19]

Chung et al.

[11] Patent Number: 5,221,675
[45] Date of Patent: Jun. 22, 1993

[54] AZA-SPIROCYCLIC COMPOUNDS THAT ENHANCE CHOLINERGIC NEUROTRANSMISSION

[75] Inventors: John Y. L. Chung, Edison, N.J.; David S. Garvey, Lake Forest, Ill.

[73] Assignee: Abbott Laboratories, Abbott Park, Ill.

[21] Appl. No.: 661,773

[22] Filed: Feb. 26, 1991

Related U.S. Application Data

[63] Continuation-in-part of Ser. No. 451,410, Dec. 15, 1989, abandoned.

[51] Int. Cl.$^5$ ................ A61K 31/445; C07D 471/10; C07D 498/10
[52] U.S. Cl. .................... 514/278; 546/19; 546/20
[58] Field of Search ............. 546/19, 20; 514/278

[56] References Cited

U.S. PATENT DOCUMENTS 5,039,804  8/1991  Feldman et al. ................ 546/223

OTHER PUBLICATIONS

Heykants et al, Chemical Abstracts, vol. 71 (1969) 122186b.

*Primary Examiner*—Richard L. Raymond
*Attorney, Agent, or Firm*—Richard A. Elder; Madhavi K. Vadnere; Steven F. Weinstock

[57] ABSTRACT

Aza-spirocyclic compounds of formula (I)

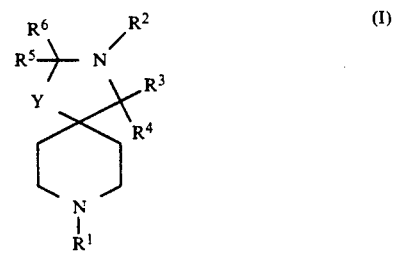

which enhance cortical cholinergic neurotransmission.

9 Claims, 8 Drawing Sheets

AZA-SPIROCYCLIC COMPOUNDS THAT ENHANCE CHOLINERGIC NEUROTRANSMISSION

CROSS REFERENCE TO RELATED APPLICATIONS

This application is a continuation-in-part of copending U.S. application Ser. No. 451,410, filed Dec. 15, 1989, now abandoned.

TECHNICAL FIELD

This invention relates to aza-spirocyclic compounds and compositions thereof which enhance cortical cholinergic neurotransmission, to processes for making such compounds, to synthetic intermediates employed in these processes and to a method of treating cognitive, neurological and mental disorders which are characterized by decreased cholinergic function, with such compounds.

BACKGROUND OF THE INVENTION

Dementia has been widely recognized as a very serious health problem. Alzheimer's Disease, which has been identified by the National Institutes of Aging as accounting for more than 50% of dementia in the elderly, is the fourth or fifth leading cause of death in Americans over 65 years of age. Four million Americans, 40% of Americans over age 85 (the fastest growing segment of the U.S. population), have Alzheimer's Disease. Twenty-five percent of all patients with Parkinson's Disease also suffer from Alzheimer's Disease. And in about 15% of cases of dementia, Alzheimer's Disease and multi-infact dementia coexist.

The precise molecular lesion(s) of the brain responsible for the morphological and functional deficits associated with Alzheimer's Disease is unclear despite intensive research efforts over the last decade. However, the most consistent abnormality found in Alzheimer's Disease, as well as in vascular dementia and cognitive impairments due to organic brain disease related directly to alcoholism (the second and third most common causes of dementia), is the degeneration of the cholinergic neurotransmitter system arising from the basal forebrain to both the cortex and hippocampus (Bigl et al., In: *Brain Cholinergic Systems*, eds. M. Steriade and D. Biesold, Oxford University Press, Oxford, 1990, pp. 364-386). Neurochemical evidence from the brains of patients afflicted with Alzheimer's Disease has revealed consistent decreases in markers of cholinergic neuronal function (Perry et al., *Br. Med. J.* 1978, 2:1457; Reisine et al., *Brain Res.* 1978, 159:477; Coyle et al., *Science* 1983, 219:1184; McGeer et al., *Neurology* 1984, 34:741). Although a number of other neurotransmitter systems are affected in Alzheimer's Disease (Davies, *Med. Res. Rev.* 1983, 3:221), the relative occurrence of such abnormalities is less consistent or the affect is less profound.

Degeneration of the cholinergic neurotransmitter system is not limited to individuals suffering from dementia, however, but has also been seen in uninflicted aged adults and rats. Decreases in cholinergic markers in the basal forebrain, decreases in cortical activities of the biosynthetic and degradative enzymes for acetylcholine, decreases in the ability to release acetylcholine from brain tissue slices, and decreases in numbers of cholinergic receptors have all been reported (for review, see Giacobini, *J. Neurosci. Res.* 1990, 27:548). Moreover, for those cholinergic neurons that remain, aging may cause a decrease in the temporal fidelity of existing impulse flow from the basal forebrain to the cortex (Aston-Jones et al., *Brain Res.* 1985, 325:271). Consistent with these findings are pharmacological studies suggesting that impairment of cholinergic mechanisms are, at least in part, responsible for the memory disturbances in aged humans and animals (Drachman and Leavitt, *Arch. Neurol.* 1974, 30:113; Bartus et al., *Science* 1982, 217:408).

Other clinical correlates associated with the neurodegenerative process of Alzheimer's Disease include decreases in cerebral blood flow and cerebral glucose utilization, which occur largely in parallel with cholinergic deficits (Ingvar and Risberg, *Exp. Brain Res.*, 1962, 3:195; Ingvar et al., Vol. 7 *Aging: Alzheimer's Disease. Senile Dementia and Related Disorders*, eds. R. Katzman, R. D. Terry, and K. L. Bick, Raven Press, 1978, p. 203; Dastur, *J. Cerebral Blood Flow & Metabol.* 1985, 5:1). In fact, it has been suggested that routine measurement of cerebral blood flow may be a useful procedure in evaluating patients suspected of having dementia, and of Alzhemimer's Disease in particular.

Conflicting opinions have been expressed in the literature about the effect of aging on resting cerebral blood flow and cerebral glucose utilization in "normal healthy" humans (Dastur, *J. Cerebral Blood Flow & Metabol.* 1985, 5:1,) and rats (Smith et al., *Brain* 1980, 103:351; Buchweitz-Milton and Weiss, *Neurobiol. Aging* 1987, 8:55), but it has been recently reported that increases in cerebral blood flow elicited by electrical stimulation of the basal forebrain in rats result in age-related impairments (Linville and Arneric, *Soc. Neurosci. Abstract* 1989, 15:17.5). Also, studies that compare the degree of learning impairment with the degree of reduced cortical cerebral blood flow in aged rats show a good correlation (Berman et al., *Neurobiol. Aging* 1988, 9:691).

Chronic alcoholism, like Alzheimer's Disease and normal aging, is also characterized by diffuse reductions in cerebral blood flow in those brain regions where cholinergic neurons arise (basal forebrain) and project to (cerebral cortex) (Lofti & Meyer, *Cerebrovasc. and Brain Metab. Rev.* 1989, 1:2). Moreover, of all the neurotransmitter systems studied, the neurotoxic effects of alcohol on the cholinergic system are thought to be the most important.

Intuitively, regardless of specific etiologic process, therapies directed towards enhancing cognitive processing would be contingent upon maintaining a well regulated balance between adequate cerebral blood flow, cerebral glucose utilization and cholinergic neurotransmission arising from the basal forebrain.

Recent clinical evidence suggests that the characteristic perfusion abnormality observed in Alzheimer's Disease patients reflects regional nicotinic cholinergic deficits (Prohovnik, *Neurobiol. Aging* 1990, 11:262). In particular, mecamylamine, a centrally acting nicotinic receptor antagonist, was found to reduce resting cortical perfusion in the parietotemporal cortex of humans, the area of the cortex most consistently found to be impaired in functional brain imaging of Alzheimer's Disease patients. In agreement with this finding, regulation of cerebral blood flow in the frontoparietal cortex, governed by the basal forebrain, is also dependent upon nicotinic mechanisms in the rat (Arneric, *J. Cerebral Blood Flow & Metabol.* 1989, 9 (Suppl. 1): S502).

Pilot clinical studies suggest that nicotine may be useful for the acute treatment of deficits in attention and information processing associated with Alzheimer's Disease (Sahakian et al., *Brit. J. Psych.* 1989, 154:797; Newhouse et al., *Psychopharmacol.* 1988, 95:171). Anecdotal evidence has suggested a negative correlation between Alzheimer's Disease and smoking, and both acutely and chronically administered nicotine were found to enhance cognitive function in rats (Levin et al., *Behav. Neural Biol.* 1990, 53:269), an effect that is preserved in aged animals (Cregan et al., 1989, 15:295.2). These clinical findings are supported by animal studies demonstrating a regenerative/protective action of chronically administered nicotine on both neuronal and vascular functions following destruction of the nigro-striatal dopamine system (Janson et al., *Prog. Brain Res.* 1989, 79:257; Owman et al., *Prog. Brain Res.* 1989, 79:267). Interestingly, in contrast to the classical down-regulation of receptors typically seen with receptor agonists, chronic nicotine administration up-regulates (50–100%) the number of acetylcholine receptors without affecting the affinity of acetylcholine for the receptor (Benwell et al., *J. Neurochem.* 1988, 50:1243). This effect occurs both in humans and smaller animals such as rats (Lapchack et al., *J. Neurochem.* 1989, 52:483).

Substantial reductions (30–50%) in nicotinic receptors have been consistently reported in the brains of patients with Alzheimer's Disease and Parkinson's Disease (Kellar et al., *Brain Res.*, 1987, 436:62; Whitehouse et al., *Neurol.* 1988, 38:720). Modest age-related reductions in cortical nicotinic receptors are also seen in otherwise healthy individuals. In addition, with chronic drug administration nicotine may work to restore receptor numbers and foster neuronal plasticity.

On the other hand, changes in muscarinic receptors are less remarkable and more dependent on receptor subtype. In fact, it has been reported that postsynaptic muscarinic acetylcholine receptors are generally preserved in Alzheimer's patients and that agonists capable of stimulating these receptors directly would be useful in correcting the cholinergic deficiency in Alzheimer's Disease and in the treatment of the memory impairment symptom of cerebral insufficiency (F.V. DeFeudis, *Drugs of Today*, 1988, 24, 473–490).

Existing cholinergic agonists, however, are therapeutically sub-optimal. This is due to unfavorable pharmacokinetics (e.g., arecoline and nicotine), poor potency and lack of selectivity (e.g., RS-86, a centrally active agonist developed by Sandoz), poor CNS penetration (e.g., carbachol) or poor oral bioavailability (e.g., nicotine). RS-86, for example, has similar affinity for cholinergic receptors located in the heart and cortical tissues and is a full agonist at cardiac receptors, whereas it is only a partial agonist at cortical receptors (S. B. Freedman, *British Journal of Pharmacology*, 1986, 87:29P). In addition, known compounds have many unwanted central agonist actions, including hypothermia, hypolocomotion and tremor. Peripheral side effects include miosis, lacrimation defecation and tachycardia (Benowitz et al., In: *Nicotine Psychopharmacology* eds. S. Wonnacott, M. A. H. Russell, & I. P. Stolerman, Oxford University Press, Oxford, 1990, pp. 112–157; M. Davidson, et al, In *Current Research in Alzheimer Therapy*; E. Giacobini and R. Becker, Ed.; Taylor & Francis: New York, 1988; pp 333–336).

Alternatively, the enhancement, via a positive allosteric modulation, of the efficacy with which the andogenous ligand, acetylcholine, binds to the nicotinic and/or the muscarinic cholinergic receptor offers significant potential for the treatment of cognitive dysfunction. Sloan and co-workers (*Life Sci.* 1985, 37:1367) suggest that the (+)isomer of (±)2-methylpiperidine enhances the binding of nicotinic ligand to rat brain receptor sites. This type of interaction can be functionally expressed by enhanced nicotinic cholinergic transmission. The advantage of such an approach is that only ongoing cholinergic neurotransmission would be enhanced, and the potential for side-effects, such as, for example, cardiovascular side effects, and dependence liabilities would be greatly diminished.

Spirocyclic compounds have been disclosed for a variety of utilities. For example, J. P. P. Heykants in *Life Sciences* 1969, 8:1029–1039, discloses 1-phenyl-1,3,8-triazaspiro[4,5]decan-2,4-dione as a major product of the metabolism of the neuroleptic drug, fluspirilene, in the rat. P. L. Feldman and M. F. Brackeen in *J. Org. Chem.* 1990, 55:4207–4209, report an improved synthesis of the analgesic, carfentanil, via the intermediate, 8-benzyl-1-phenyl-1,3,8-triazaspiro[4,5]decane-2,4-dione, by a modified Strecker synthesis and G. Winters, et al. in *Farmaco, Ed Sci.* 1970, 25:681–693, disclose the preparation of spirohydantoins, including the 1′,3′-diphenylspirohydantoin derivative of N-butyl-4-piperidone, by a modified Strecker synthesis. Also, Ugi, et al. in *Liebig's Ann.* 1963, 666:54–61 and *Ang. Chem*, 1962, 74:9–21, described the preparation of spirohydantoin derivatives of cyclohexanone and U.S. Pat. No. 4,162,246, issued Jul. 24, 1979, and assigned to Sankyo Company Limited, is representative of a series of patents and publications authored by Sankyo scientists describing the preparation of oligiomeric spirohydantoin derivatives of 2,2,6,6-tetraalkylpiperidine and their use as polymer stabilizers. However, these references describing the synthesis of spirocyclic hydantoins do not suggest the novel compounds of the present invention which interact with and enhance central cholinergic neurotransmission.

Several other references have shown spirocyclic piperidines which have central nervous system utility, but disclose compounds which are chemically quite different from our novel compounds. French Patent 1,291,532, assigned to Sandoz S. A., discloses substituted spirosuccinimides of the formula

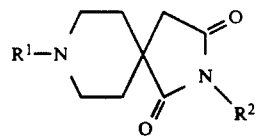

wherein R[1] and R[2] are each hydrogen or lower alkyl, including the compound, 3-ethyl-8-methyl-2,8-diazaspiro[4,5]decane-1,3-dione (referred to herein as RS-86), having parasympathicomimetic activity. Bollinger, U.S. Pat. No. 4,735,944, issued Apr. 5, 1988, discloses spirodioxolanes, spirodithiolanes and spiro-oxothiolanes for use in mental therapy and Tsukamoto, et al., European Patent Application No. EP0311313, published Apr. 12, 1989, discloses heterocyclic spiro compound which act upon muscarinic acetylcholine receptors.

SUMMARY OF THE INVENTION

The present invention is directed to compounds that enhance cortical cholinergic neurotransmission of formula (I):

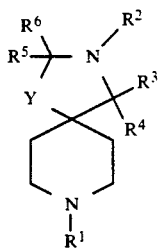

or pharmaceutically acceptable salts thereof, wherein
R$^1$ is hydrogen or methyl;
Y is O or

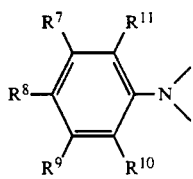

wherein R$^7$, R$^8$, R$^9$, R$^{10}$ and R$^{11}$ are independently selected from the group consisting of
(i) hydrogen
(ii) halogen,
(iii) methyl,
(iv) halomethyl,
(v) methoxy and
(vi) ethoxy, or
R$^7$ and R$^8$ or R$^8$ and R$^9$ or R$^9$ and R$^{10}$ or R$^7$ and R$^{11}$ taken together are methylenedioxy;
R$^2$ is hydrogen or methyl, R$^3$ and R$^4$ taken together form =O, and R$^5$ and R$^6$ taken together form =O or =S when Y is

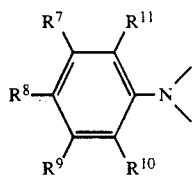

wherein R$^7$, R$^8$, R$^9$, R$^{10}$ and R$^{11}$ are as defined above, or
R$^2$ is

wherein Z is O or S, R$^3$ and R$^4$ are both hydrogen, R$^5$ is methyl and R$^6$ is hydrogen when Y is O;
subject to the proviso that R$^1$, R$^2$, R$^7$, R$^8$, R$^9$, R$^{10}$ and R$^{11}$ are not all hydrogen at the same time.

The present invention is also directed to pharmaceutical compositions comprising a therapeutically-effective amount of a compound of formula (I) and a pharmaceutically-acceptable carrier or diluent, as well as to a method of treating cognitive, neurological and mental disorders, which are characterized by decreased cholinergic function in humans and lower mammals, by administration of a compound of formula (I).

DETAILED DESCRIPTION OF THE INVENTION

Figure 1:
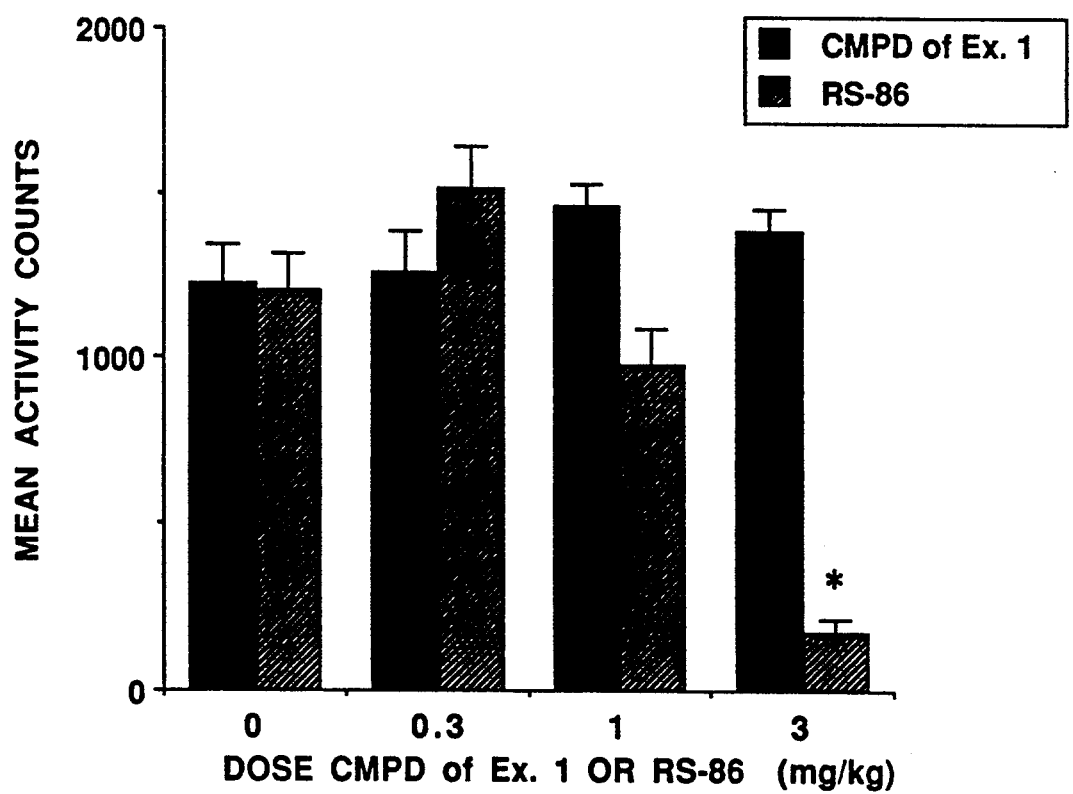
FIG. 1 is a graphical representation (bar graph) of the effects of the compound of Example 1 and RS-86 on CD1 mouse locomotor activity as a function of dose.
Figure 2:
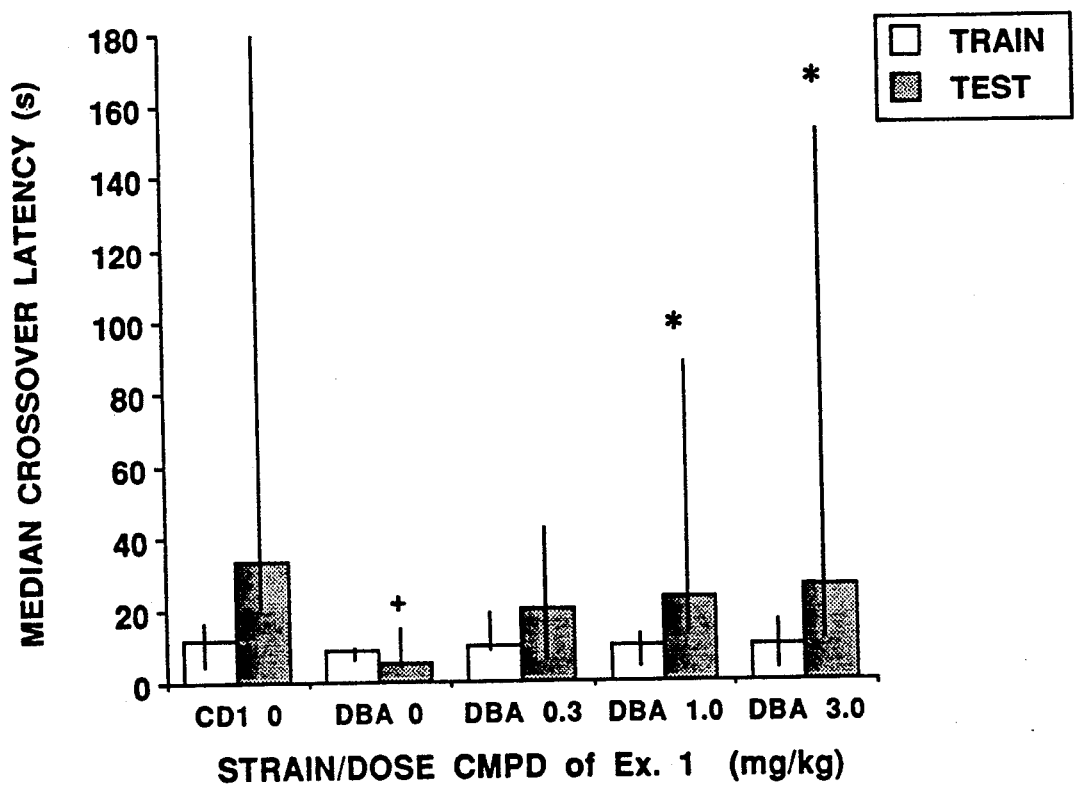
FIG. 2 is a graphical representation (bar graph) of the effects of the compound of Example 1 on the performance of CD1 and DBA mice in inhibitory avoidance studies expressed as median crossover latency time.

This invention relates to novel aza-spirocyclic compounds of formula (I) which enhance cortical cholinergic neurotransmission and, therefore, may be used in the treatment of cognitive, neurological and mental disorders characterized by decreased cholinergic function, such as, for example Alzheimer's Disease.

In particular the invention relates to compounds of formula (I):

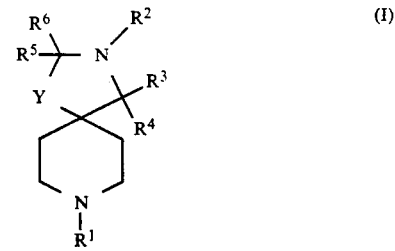

or pharmaceutically acceptable salts thereof, wherein
R$^1$ is hydrogen or methyl;
Y is O or

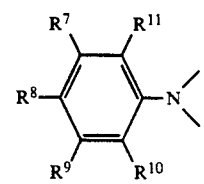

wherein $R^7$, $R^8$, $R^9$, $R^{10}$ and $R^{11}$ are independently selected from the group consisting of
(i) hydrogen
(ii) halogen,
(iii) methyl,
(iv) halomethyl,
(v) methoxy and
(vi) ethoxy, or $R^7$ and $R^8$ or $R^8$ and $R^9$ or $R^9$ and $R^{10}$ or $R^7$ and $R^{11}$ taken together are methylenedioxy;

$R^2$ is hydrogen or methyl, $R^3$ and $R^4$ taken together form =O, and $R^5$ and $R^6$ taken together form =O or =S when Y is

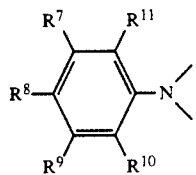

wherein $R^7$, $R^8$, $R^9$, $R^{10}$ and $R^{11}$ are as defined above, or $R^2$ is

wherein Z is O is O or S, $R^3$ and $R^4$ are both hydrogen, $R^5$ is methyl and $R^6$ is hydrogen when Y is O; subject to the proviso that $R^1$, $R^2$, $R^7$, $R^8$, $R^9$, $R^{10}$ and $R^{11}$ are not all hydrogen at the same time.

In one embodiment of the present invention are compounds, represented by formula (Ia), wherein $R^2$ is is

Z is as defined above and Y is O:

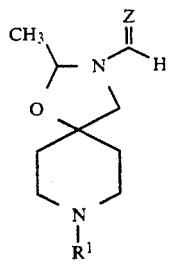

(Ia)

In another embodiment of the present invention, represented by formula (Ib), Y is

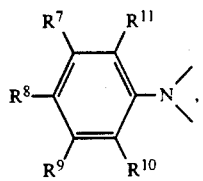

$R^3$ and $R^4$ taken together form =O, $R^5$ and $R^6$ taken together form =O or =S and $R^7$, $R^8$, $R^9$, $R^{10}$ and $R^{11}$ are as defined above:

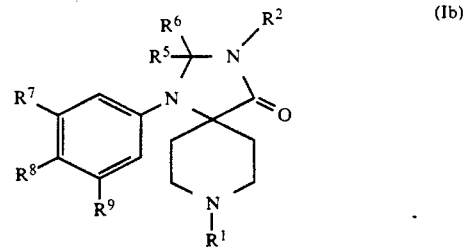

(Ib)

The following are representative compounds of the present invention:
2,8-dimethyl-1-oxa-3-formyl-3,8-diazaspiro[4,5]decane;
2-methyl-1-oxa-3-formyl-3,8-diazaspiro[4,5]decane;
2,8-dimethyl-1-oxa-3-thioformyl-3,8-diazaspiro[4,5]decane;
2-methyl-1-oxa-3-thioformyl-3,8-diazaspiro[4,5]decane,
3-methyl-1-phenyl-1,3,8-triazaspiro[4,5]decane-2,4-dione;
8-methyl-1-phenyl-1,3,8-triazaspiro[4,5]decane-2,4-dione;
3,8-dimethyl-1-phenyl-1,3,8-triazaspiro[4,5]decane-2,4-dione;
3-methyl-1-phenyl-1,3,8-triazaspiro[4,5]decane-2-thio-2,4-dione;
8-methyl-1-phenyl-1,3,8-triazaspiro[4,5]decane-2,4-dione;
3,8-dimethyl-1-phenyl-1,3,8-triazaspiro[4,5]decane-2-thio-2,4-dione;
as well as pharmaceutically-acceptable salts thereof.

The term "halogen" as used herein refers to bromo (Br), chloro (Cl), fluoro (F) and iodo (I).

The term "halomethyl" as used herein refers to a methyl group bearing at least one halogen substituent, for example, chloromethyl, fluoromethyl, bromomethyl, trifluoromethyl and the like.

Compounds of the invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. In addition, some of the compounds of the invention can exist as exo and endo isomers. It is to be understood that the present invention anticipates and includes within its scope all such isomers and mixtures thereof. The terms "R" and "S" configuration used herein are as defined by IUPAC 1974 Recommendations for Section E, Fundamental Stereochemistry, *Pure Appl. Chem.*, 1976, 45: 13-30.

The compounds of the present invention may be synthesized as shown in reaction schemes I, II and III presented below, in which Y, Z, $R^1$, $R^2$, $R^3$, $R^4$, $R^5$, $R^6$, $R^7$, $R^8$ and $R^9$ are as defined above for formula (I) and $R^{12}$ is a nitrogen protecting group, using the reactions and techniques described in this section. the reactions are performed in a solvent appropriate to the reagents and materials employed are suitable for the transformation being effected. It is understood by those skilled in the art of organic synthesis that the functionality present on the phenyl ring and other portions of the molecule must be consistent with the chemical transformation proposed. This will, on occasion, necessitate judgment as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of amino-protecting groups is well known in the art for protecting amino groups against undersirable reactions during a synthetic procedure and many such protecting groups are known, c.f., T. H. Greene, *Protective Groups in Organic Synthesis*, John Wiley & Sons, New York (1981).

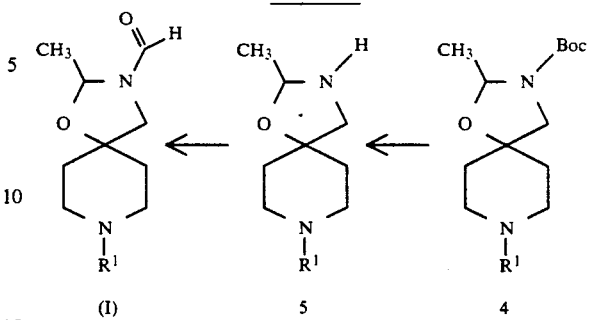

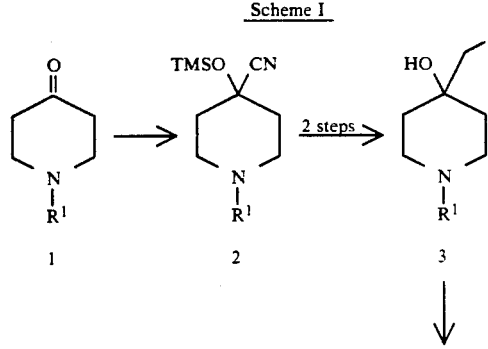

Scheme I

According to reaction scheme I, an N-protected piperidone compound of formula 1 is treated with trimethylsilyl cyanide (TMSCN), preferably in the presence of a catalytic amount of zinc iodide, to afford the protected cyanohydrins of formula 2. The cyanohydrins of formula 2 are, in turn, reduced to the corresponding amino alcohols which are treated with a suitable reagent for protecting the amino group, for example, di-t-butyl-dicarbonate (Boc-anhydride), in the presence of a suitable base such as sodium bicarbonate to afford the compounds of formula 3. The compounds of formula 3 are then treated with an acetaldehyde acetal, such as diethyl or dimethyl acetal, in the presence of a suitable acid, for example p-toluenesulfonic acid or a Lewis acid, such as boron trifluoride etherate, to afford the spiro-cyclic compounds of formula 4. The compounds of formula 4 are treated with a suitable reagent for removing the N-protecting group, for example trifluoroacetic acid, to afford the compounds of formula 5. The compounds of formula 5 are finally, in turn, treated with a suitable acylating agent such as p-nitrophenyl formate or thioformate to afford the compounds of formula (I).

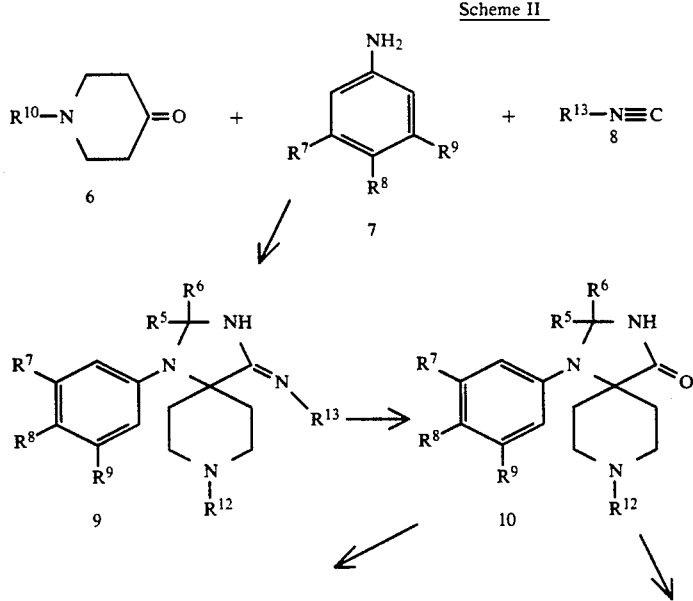

-continued
Scheme II

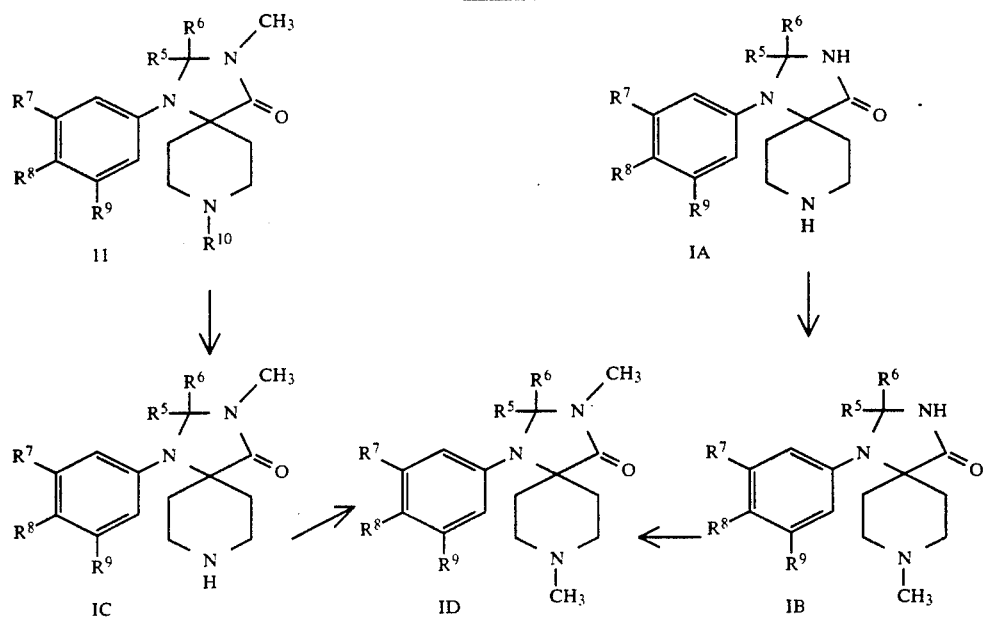

Scheme II

According to reaction scheme II, using the method of Ugi, et al. (*Liebigs Ann.* 1963, 666:54–61 and *Angew. Chem.*, 1962, 74:9–22), an N-protected piperidinone of formula 6 is condensed with an isocyanide of formula 8, an amine of formula 7 and potassium isocyanate or potassium thioisocyanate to afford a compound of formula 9. Preferably, the isocyanide is cyclohexyl isocyanide ($R^{13}$=cyclohexyl) and the N-protecting group ($R^{12}$) is benzyl. The imine group is then hydrolyzed to the ketone, as described by Ugi, et al. (ibid), affording a compound of formula 10, using a suitable acid or base catalyst, for example, hydrochloric acid or potassium hydroxide. A compound of formula 10 may then be treated with a suitable reagent for removing the amino-protecting group to afford a compound of formula IA. For example, a benzyl group is preferably removed by catalytic hydrogenolysis using a suitable catalyst, such as palladium on carbon. A compound of formula IA is then methylated using standard methylation procedures, for example, formic acid and formaldehyde, to afford a compound of formula IB. Alternately, a compound of formula 10 is methylated by standard procedures, for example, using dimethylsulfate or methyl iodide in the presence of a base such as sodium hydroxide, sodium hydride or potassium carbonate or, or using diazomethane, to afford a compound of formula 11, which is, in turn, deprotected to afford a compound of formula IC. A compound of formula IC may be further methylated by standard procedures, for example, by using dimethylsulfate or methyl iodide in the presence of a base, such as sodium hydroxide, sodium hydride or potassium carbonate, or by treatment with formic acid and formaldehyde, to afford a compound of formula ID.

Scheme III

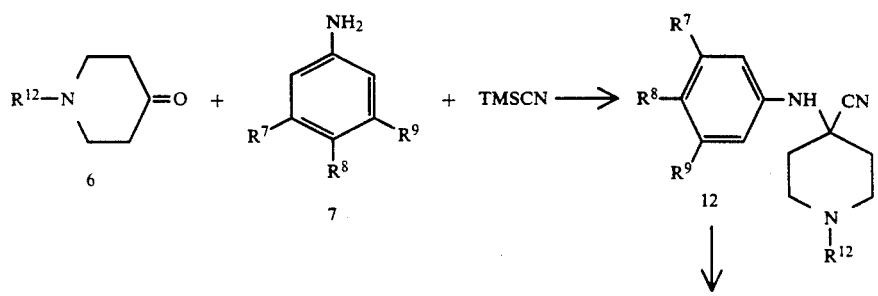

Scheme III

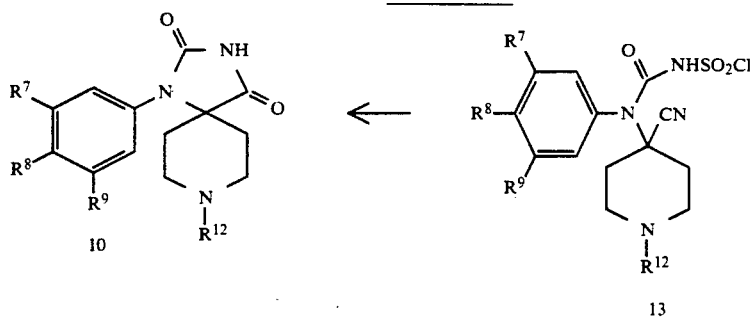

Scheme III

The intermediate compound 10, wherein $R^{12}$ is benzyl, may be prepared by the method described by P. L. Feldman and M. F. Brackeen in *J. Org. Chem*, 1990, 55:4207-4209, as shown in reaction scheme III. According to this method, N-benzyl-4-piperidinone is reacted with an aniline compound of formula 7 and trimethylsilyl cyanide (TMSCN) under anhydrous conditions, preferably in glacial acetic acid, to afford a compound of formula 12. A compound of formula 12, in turn, is treated with chlorosulfonyl isocyanate, to afford a compound of formula 13, which may then be cyclized under acidic conditions, for example, by refluxing in aqueous hydrochloric acid followed by cooling and pH adjustment to approximately 5.5, to afford a hydantoin compound of formula 10. Compounds of formula 10 are key intermediates in the preparation of the compounds of formula (I).

The following examples, which are provided for illustration and not limitation of the invention, will serve to further illustrate preparation of the novel compounds of the invention. Thin-layer chromatography (TLC) was performed on 0.25 mm E. Merck precoated silica gel plates (60 F-254). Flash chromatography was performed on 200-400 mesh silica gel (E. Merck).

EXAMPLE 1

2,8-Dimethyl-1-oxa-3-formyl-3,8-diazaspiro[4,5]decane hydrogen oxalate

Step A:
4-Cyano-4-trimethylsilyloxy-1-methyl-piperidine

To a mixture of N-methyl-4-piperidone (10.0 g, 88.3 mmol) and zinc iodide (10 mg) was added trimethylsilyl cyanide (9.64 g, 97.2 mmol) at 0° C. The reaction mixture was allowed to warm to ambient temperature and then heated at 60° C. for 18 hours. After stirring at ambient temperature for 2 days, the reaction mixture was fractionally distilled to give 13.5 g (72% yield) of the desired trimethylsilyl ether cyanohydrin, b.p. 66°-72° C./1.3 mmHg; TLC $R_f$=0.49 (10% methanol in chloroform); MS(Cl) m/e 213 (M+H)+; $^1$H NMR (CDCl$_3$, 300 MHz) δ2.67 (br m, 2H), 2.35 (m, 2H), 2.30 (s, 3H), 2.09 (m, 2H), 1.90 (ddd, J=15.0, 10.2, 3.6 Hz, 2H), 0.25 (s, 9H).

Step B:
4-Hydroxy-4-tert-butoxycarbonylaminomethyl-1-methyl-piperidine

To a solution of lithium aluminum hydride (33.1 mL of 1M solution in THF, 33.1 mmol) in tetrahydrofuran (THF) was added a solution of the trimethylsilyl ether cyanohydrin from Step A (6.39 g, 30.1 mmol) in THF (15 mL) at 0° C. under nitrogen. After stirring overnight at ambient temperature, the reaction mixture was quenched with 1.3 mL water (diluted with THF), 1.5 mL of 2N aqueous sodium hydroxide solution, followed by 4 mL water and let stirred for 24 hours. The slurry was filtered through sodium sulfate/Celite ® filter aid and the filtrate concentrated to give the crude primary amine. This was taken up in methanol (50 mL) and treated with solid sodium bicarbonate (3.33 g, 38.6 mmol) and di-t-butyl-dicarbonate ((Boc)$_2$O:7.22 g, 33.1 mmol) slowly. After stirring overnight, the reaction mixture was concentrated to dryness. The residue was treated with saturated aqueous sodium bicarbonate solution and extracted with chloroform (5×). The extract was dried over anhydrous sodium sulfate, filtered, concentrated under resduced pressure and purified by flash chromatography (10% MeOH in CHCl$_3$/NH$_4$OH=1000:5→1000:10) to give 4.74 g (50% yield) of 4-trimethylsilyloxy-4-tert-butoxycarbonylaminomethyl-1-methyl-piperidine as an oil; TLC $R_f$=0.15 (10% methanol in chloroform; MS(Cl) m/e 317 (M+H)+; $^1$H NMR (CDCl$_3$, 300 MHz) δ4.71 (br s, 1H, D$_2$O exchangeable), 3.20 (d, J=5.9 Hz, 1H), 2.50-2.35 (m, 4H), 2.28 (s, 3H), 1.68 (m, 4H), 1.44 (s, 9H), 0.15 (s, 9H)) and 3.28 g (45%) of 4-hydroxy-4-tert-butoxycarbonylaminomethyl-1-methyl-piperidine as a solid; TLC $R_f$=0.04 (10% methanol in chloroform); MS(Cl) m/e 245 (M+H)+; $^1$H NMR (CDCl$_3$, 300 MHz) d 4.61 (brs, 1H, D$_2$O exchangeable) 3.14 (d, J=6.3 Hz, 2H), 2.62-2.50 (m, 2H), 2.34 (m, 2H), 2.30 (s, 3H), 1.61 (m, 4H), 1.44 (s, 9H).

Step C:
2,8-Dimethyl-1-oxa-3-tert-butoxycarbonyl-3,8-diazaspiro[4.5]decane

A solution of 4-hydroxy-4-tert-butoxycarbonylaminomethyl-1-methyl-piperidine (3.27 g, 13.38 mmol), acetaldehyde diethyl acetal (3.95 g, 33.46 mmol) and p-toluenesulfonic acid hydrate (3.05 g, 16.06 mmol) in acetonitrile (70 mL) was heated at 90° C. in an open flask. The acetaldehyde diethyl acetal was added freely until complete consumption of starting material. The reaction mixture was washed with saturated aqueous potassium carbonate solution and extracted with chloroform (4×). The extract was dried over anhydrous sodium sulfate, filtered, concentrated under reduced pressure and the crude product was purified by flash chromatography (10% methanol in chloroform/ammonium hydroxide=1000:2) to give 2.25 g (62% yield) of the title compound as an amber oil; TLC $R_f$=0.15

(10% methanol in chloroform/ammonium hydroxide=9.9:0.1); MS(Cl) m/e 271 (M+H)+.

Step D: 2,8-Dimethyl-1-oxa-3,8-diazaspiro[4.5]decane

A solution of the product from Step C (2.15 g, 7.95 mmol) and trifluoroacetic acid (8 mL) in methylene chloride (8 mL) was stirred for 1 hour at ambient temperature. After concentration, basification with saturated aqueous potassium carbonate solution and continuous-extraction with chloroform overnight, the organic phase was dried over anhydrous sodium sulfate, filtered and concentrated in vacuo to gave 1.25 g (92% yield) of the desired product as an amber oil. TLC $R_f$=0.19 (chloroform/methanol/ammonium hydroxide=10:4:1). MS(Cl) m/e 171 (M+H)+. $^1$H NMR (CD$_3$OD, 300 MHz) d 4.55 (q, J=5.5 Hz, 1H), 3.01 (d, J=11.8 Hz, 1H), 2.71 (d, J=11.8 Hz, 1H), 2.49 (m, 4H), 2.27 (s, 3H), 1.80-1.50 (m, 4H), 1.32 (d, J=5.5 Hz, 3H).

Step E:
2,8-Dimethyl-1-oxa-3-formyl-3,8-diazaspiro[4.5]decane

To a solution of the product from Step D (220 mg, 1.29 mmol) and triethylamine (314 mg, 3.10 mmol) in methylene chloride (3 mL) was added p-nitrophenyl formate (518 mg, 3.10 mmol) at ambient temperature. After stirring for 2 days, the reaction mixture was washed with saturated aqueous potassium carbonate solution and extracted with chloroform (4×). The combined organic phase was dried over anhydrous sodium sulfate, filtered, concentrated and flash chromatographed (CHCl$_3$:MeOH:NH$_4$OH=90:10:0.5) to give 68 mg (27% yield) of amber oil. This was treated with oxalic acid (31 mg) in diethyl ether and crystallized from ethanol/diethyl ether to give 81 mg of white solid, m.p. 137°-138° C.; TLC $R_f$=0.30 (10% methanol in chloroform/ammonium hydroxide=9.9:0.1); MS(Cl) m/e 199 (M+H)+.; $^1$H NMR (C$_3$DOD, 300 MHz) (2 conformers: 45:55) δ8.24 (br s, 1H), 5.43 (q, J=5.5 Hz, 0.45H), 5.36 (q, J=5.2 Hz, 0.55H), 3.83 (br d, J=11.8 Hz, 0.45H), 3.67 (br d, J=11.8 Hz, 0.45H), 3.43, (d, J=11.8 Hz, 0.55H), 3.36 (d, J=11.8 Hz, 0.55H), 3.31 (m, 4H), 2.88 (s, 1.65H), 2.87 (s, 1.35H), 2.25-1.85 (m, 4H), 1.53 (d, J=5.2 Hz, 1.65H), 1.43 (d, J=5.2 Hz, 1.35H). Analysis Calculated for C$_{10}$H$_{18}$H$_2$O$_2$. C$_2$H$_2$O$_4$. 0.2 H$_2$O: C, 49.38; H, 7.04; N, 9.60. Found: C, 49.54; H, 6.97; N, 9.50.

EXAMPLE 2

2,8-Dimethyl-1-oxa-3-thioformyl-3,8-diazaspiro[4,5]-decane hydrogen oxalate

The title compound may be prepared from the product of Example 1, Step D, according to the method reported by Lawesson, et al. in Bull. Soc. Chim. Belg. 1978, 87:229. The dimer of p-methoxyphenylthionophosphine sulfide is added to a solution of 2,8-dimethyl-1-oxa-3,8-diazaspiro[4.5]decane, the product of Step D of Example 1, in toluene and the reaction mixture is heated to from 85° C. to 110° C. for several hours under an inert atmosphere. The toluene is then removed in vacuo and the residue purified by flash chromatography on silica gel to afford the title compound.

EXAMPLE 3

3-Methyl-1-phenyl-1,3,8-triazaspiro[4,5]decane-2,4-dione hydrochloride

Step A:
8-Benzyl-4-cyclohexylimino-1-phenyl-1,3,8-triazaspiro[4,5]decane-2-one

The title compound was prepared by the method of Ugi, et al. (Liebig's Ann., 1963, 666:54-61). 1-Benzyl-4-piperidinone (94.5 g, 0.5 mol) and cyclohexylisonitrile (54.5 g, 0.45 mol), both commercially available from Aldrich Chemical Company, were dissolved in 250 mL of methanol at ambient temperature. A solution of potassium cyanate (40.5 g, 0.5 mol) in 100 mL of water was added in one portion with stirring. Aniline hydrochloride was added in portions over a 45 minute period and the reaction mixture was allowed to stir at ambient temperature overnight. Hexane and diethyl ether were added to the reaction mixture until a solid formed. The solid was filtered and washed with diethyl ether and water. The solid was then triturated with four 1 L portions of boiling water and crystallized from methanol to give 50.6 g (27% yield) of the title compound, m.p. 208°-210° C.

Step B:
8-Benzyl-1-phenyl-1,3,8-triazaspiro[4,5]decane-2,4-dione

Potassium hydroxide (50.4 g, 0.9 mol) was added to 300 mL of ethylene glycol followed by 8-benzyl-4-cyclohexylimino-1-phenyl-1,3,8-triazaspiro[4,5]decane-2-one (37.7 g, 0.11 mol) from Step A. The reaction mixture was heated slowly to a gentle reflux and 100 mL of solvent was removed by distillation over a 4.5 hour period. The reaction mixture was then cooled in ice to 50° C. and poured into water (500 mL). The aqueous solution was adjusted to approximately pH 8-9 by adding concentrated hydrochloric acid while cooling in ice. The precipitate was filtered and washed with water to give 25.8 g of solid. The solid was crystallized from boiling chloroform to give 19.45 g of the title compound, m.p. 159°-160° C.

Step C: Mixture of
8-benzyl-3-methyl-1-phenyl-1,3,8-triazaspiro[4,5]decane-2,4-dione and
8-benzyl-1-phenyl-1,3,8-triazaspiro[4,5]decane-2,4-dione 8-Benzyl-1-phenyl-1,3,8-triazaspiro[4,5]decane-2,4-dione (25.6 g (76 mmol), from Step B, potassium carbonate (52.44 g, 0.38 mol) and dimethyl sulfate (9.6 g, 76 mmol) were combined in 250 mL of N,N-dimethylformamide (DMF) and the reaction mixture was heated to 60° C. The reaction mixture was heated at 60° C. for 4 hours and then concentrated in vacuo. Water was added to the residue and the aqueous mixture was extracted with two portions of diethyl ether. The ether extracts were washed with two portions of water, dried over anhydrous magnesium sulfate, filtered and concentrated in vacuo. The residue was triturated with diethyl ether and washed with ether to give a solid which was crystallized from diethyl ether containing a small amount of anhydrous ethanol to give a crystalline solid, m.p. 122°-126° C. The filtrate was treated with activated charcoal, filtered and concentrated to 100 mL. Hexane was added until crystals were formed. The crystals were collected by filtration and washed with hexane to give a crystalline solid, m.p. 123°–126° C. The crystals were combined and recrystallized from diethyl ether/acetone/hexane to give 16.6 g (63% yield) of the title compound, m.p. 127°–130° C.

Step D:
8-Benzyl-3-methyl-1-phenyl-1,3,8-triazaspiro[4,5]decane-2,4-dione

The mixture from Step C (0.98 g) was separated by flash chromatography on silica gel, eluting with 1% methanol in chloroform to give 1.0 g of the title compound as a clear colorless oil which solidified to an opaque solid on standing at ambient temperature; TLC (methanol/chloroform, 1:40) $R_f$ 0.43; MS (DCl/NH$_3$) M/Z: 260 (M+2H-Bn)$^+$, 277 (M+2H+NH$_3$-Bn)$^+$, 350 (M+H)$^+$, 367 (M+NH$_4$)$^+$; 300 MHz $^1$H NMR (CDCl$_3$) $\delta$1.80–1.88 (m, 2H), 1.94 (td, J=5, 12 Hz, 2H), 2.69–2.77 (m, 2H), 2.83 (td, J=3, 12 Hz, 2H), 3.09 (s, 3H), 3.53 (s, 2H), 7.14–7.20 (m, 2H), 7.20–7.29 (m, 5H), 7.41–7.48 (m, 3H).

Step E:
3-Methyl-1-phenyl-1,3,8-triazaspiro[4,5]decane-2,4-dione hydrochloride

To a solution of 8-benzyl-3-methyl-1-phenyl-1,3,8-triazaspiro[4,5]decane-2,4-dione (470 mg, 1.3 mmol), from Step D, in methanol (100 mL) were added concentrated aqueous hydrochloric acid (0.12 mL, 1.4 mmol) and wet 20% palladium on carbon (0.47 g). The reaction vessel was pressurized with hydrogen (4 atmospheres) and shaken on a Parr apparatus at ambient temperature for 2 hours. The reaction mixture was then filtered sequentially through a paper filter and through a PTFE (polytetrafluoroethylene) filter membrane (0.45μ), rinsing with methanol. The filtrate was concentrated under reduced pressure and then the residue was dried to give 0.34 g (89% yield) of the title compound as a white solid, m.p. >330° C. (dec); MS (DCl/NH$_3$) M/Z: 260 (M+H)$^+$, 277 (M+NH$_4$)$^+$; 300 MHz $^1$H NMR (CDCl$_3$) $\delta$2.02 (td, J=5, 14 Hz, 2H), 2.31 (d, J=15 Hz, 2H), 3.08 (s, 3H), 3.34–3.43 (m, 2H), 3.72 (td, J=3, 12 Hz, 2H), 7.29–7.35 (m, 2H), 7.49–7.58 (m, 3H).

EXAMPLE 4

3,8-Dimethyl-1-phenyl-1,3,8-triazaspiro[4,5]decane-2,4-dione

To a flask containing a sample of 3-methyl-1-phenyl-1,3,8-triazaspiro[4,5]decane-2,4-dione hydrochloride (100 mg, 0.34 mmol), the product of Example 3, cooled in an ice-water bath, were added 88% aqueous formic acid solution (0.6 mL) and 37% aqueous formaldehyde solution (0.10 mL). A water-cooled spiral condenser was added to the flask and the reaction mixture was heated, with stirring, overnight in an oil bath at 80° C. The reaction mixture was then diluted with water (5 mL), acidified with 1.0M aqueous hydrochloric acid solution (0.5 mL) and extracted with 2×5 mL of diethyl ether. The aqueous phase was chilled and made basic by the addition of 2.0M aqueous sodium hydroxide solution (1.0 mL). The basic solution was continuously extracted, overnight, with ethyl acetate. The ethyl acetate extract was concentrated and the residue was dissolved in methylene chloride. The methylene chloride solution was dried over anhydrous sodium sulfate, filtered and concentrated under reduced pressure to give 116 mg of a white solid. The solid was purified by flash chromatography on silica gel, eluting with 7.5% methanol in chloroform to give 85 mg (91% yield) of the title compound as opaque white crystals, m.p. 132°–134° C.; TLC (10% methanol in chloroform) $R_f$ 0.43; MS (DCl/NH$_3$) M/Z: 274 (M+H)$^+$, 291 (M+NH$_4$)$^+$; 300 MHz $^1$H NMR (CDCl$_3$) $\delta$1.81–1.89 (m, 2H), 1.98 (td, J=5, 13 Hz, 2H), 2.31 (s, 3H), 2.66–2.74 (m, 2H), 2.81 (td, J=3, 12 Hz, 2H), 3.10 (s, 3H), 7.14–7.19 (m, 2H), 7.39–7.47 (m, 3H). Analysis calculated for $C_{15}H_{19}N_3O_2 \cdot 0.1H_2O$: C, 65.47; H, 7.05; N, 15.27. Found: C, 65.38; H, 6.91; N, 15.12.

UTILITY

The compounds of formula (I) enhance cortical cholinergic neurotransmission and, therefore, are useful in treatment of cognitive disorders or neurological and mental illnesses-characterized dysfunction of the cholinergic system. Such diseases include presenile and senile dementia, Alzheimer's Disease, tardive dyskinesia, hyperkinesia, mania and acute confusion disorders. The compounds of this invention may also be useful analgesic agents and are therefore useful in the treatment of severe painful conditions such as rheumatism, arthritis, and terminal illnesses.

For the purpose of identifying compounds as cholinergic agonists/modulators which are capable of interacting with acetylcholine receptors, ligand-receptor binding assays were carried out as an initial screen. The ability of the compounds of the invention to interact with cholinergic receptors and to act as cholinergic agonists/modulators can be demonstrated in vitro using the following protocols.

BIOLOGICAL ACTIVITY OF EXAMPLE 1

In Vitro Determination of Muscarinic Receptor Binding Potencies

Protocols For Determination of Muscarinic Receptor Binding Potencies of Agonists The potencies of agonist binding at central muscarinic M1 and M2 muscarinic binding sites were determined by analysis of competition with specific muscarinic receptor radioligands. The cerebral cortical M1 receptor was identified with [$^3$H]pirenzepine. The muscarinic receptors of the ponsmedulla are M2 in nature and were identified with [$^3$H]quinuclidinyl benzilate (QNB). Adult rat fronto-parietal cortex and ponsmedulla were dissected free on an ice-block and homogenized (1:200 w/v) in 50 mM sodium-potassium phosphate buffer (pH 7.4) with a polytron. Competition between various concentrations of agonist molecules and 6 nm [$^3$H]pirenzepine (with 0.5 mg/mL cortical membranes) of 0.2 nM [$^3$H]QNB (with 0.5 mg/mL ponsmedulla membranes) was performed at 25° C. in an assay volume of 1 mL. After 60–75 minutes, the bound radioligand was separated by vacuum filtration on Whatman GF/B glass fiber filters. Non-specific binding was defined as radioactivity remaining in the presence of 10 uM atropine. Competition curves were analyzed with a four-parameter logistic program on a computer. The Ki value for the agonist was determined after correction of the IC$_{50}$ value for the presence of the radioligand.

TABLE 1

| COMPOUND | Ki (mM) @ M1 RECEPTOR | Ki (mM) @ M2 RECEPTOR |
| --- | --- | --- |
| Example 1 | 32 | 30 |

These results indicate that the compound of Example 1 binds to both M1 and M2 muscarinic receptors.

In Vitro Determination of Agonist Intrinsic Activity at Central Muscarinic Receptor Effector Systems

Protocol for the Determination of Agonist Intrinsic Activity at Central Muscarinic Receptor-Effector Systems To show that the novel molecules were indeed muscarinic agonists in brain tissue, a pharmacological response assay employing rat striatum was employed. Rat striatal muscarinic receptors are coupled to the inhibition of the conversion of adenosine triphosphate (ATP) to cyclic adenosine monophosphate (cAMP). This method is described in detail in D. J. Anderson and M. McKinney, *Brain Res*, 1988, 475:28–34. The ATP stores in dissociated rat striatum were labeled with [$^3$H]adenine and [$^3$H]-cAMP levels were elevated with 10 um forskolin. Muscarinic receptor activation with the agonist carbachol inhibits forskolin-activated levels of [$^3$H]cAMP by about 40%. Most agonists stimulate this receptor-effector system with $EC_{50}$ values in the range of 0.1–10 uM. Intrinsic activities (maximal responses relative to that of the full agonist carbachol) can thus be measured at 100 uM. Agonist activation of this biochemical response is expressed as percent activity measured at 100 uM relative to that of 100 uM carbachol. All responses were shown to be fully blocked by the selective muscarinic antagonist atropine.

TABLE 2

| COMPOUND | INTRINSIC ACTIVITY (% relative to carbacol) |
| --- | --- |
| Example 1 | 53 |

These results indicate that the compound of Example 1 is a central muscarinic receptor agonist with partial agonist activity.

In Vivo Studies Demonstrating Activity as Cognition Enhancers

A. Inhibitory Avoidance Studies

The inhibitory (or sometimes called passive) avoidance (IA) test is a well accepted animal model of learning/memory used to assess the activity of novel muscarinic agonists to enhance cognitive function (Wanibuchi et al., *Eur. J. Pharmacol.*, 1990, 187:479). Animals are placed in the illuminated (12×14×11 cm) portion of a two-chambered box, from which they enter through a guillotine door to the larger (24×13.5×12 cm) dark compartment of the box. Entry to the dark compartment is accompanied by a mild (0.5 mA), brief (2 seconds) footshock. Initial latencies to cross are recorded, with an imposed 60 second ceiling. Following a 72 hour retention interval, animals are returned to the illuminated chamber, and latency to return to the dark compartment is again recorded, with a ceiling of 180 seconds. No footshock is administered on the test day.

Previous studies have indicated a retention deficit in DBA versus CD1 mice in the 72 hour retention model. Accordingly, adult male DBA mice (n=~15/group) were injected with either the compound of Example 1 or the reference standard RS-86 (0, 0.3, 1.0, or 3.0 mg/kg, i.p.) approximately 45 minutes prior to the training described above. Saline-treated adult male CD1 mice (n=15) served as controls.

FIG. 1 demonstrates that latencies were equivalent across all groups of animals dosed with the compound of Example 1. At the 72 hour retention test, untreated DBA mice showed a significant retention deficit relative to CD1 controls (Mann-Whitney U=196, z=2.42, p<0.01). In contrast, animals treated with the compound of Example 1 @1.0 or 3.0 mg/kg showed a significant attenuation of the observed retention deficit (U=171.5 & 172, z=2.04 & 2.0 respectively, p<0.05).

Figure 3:
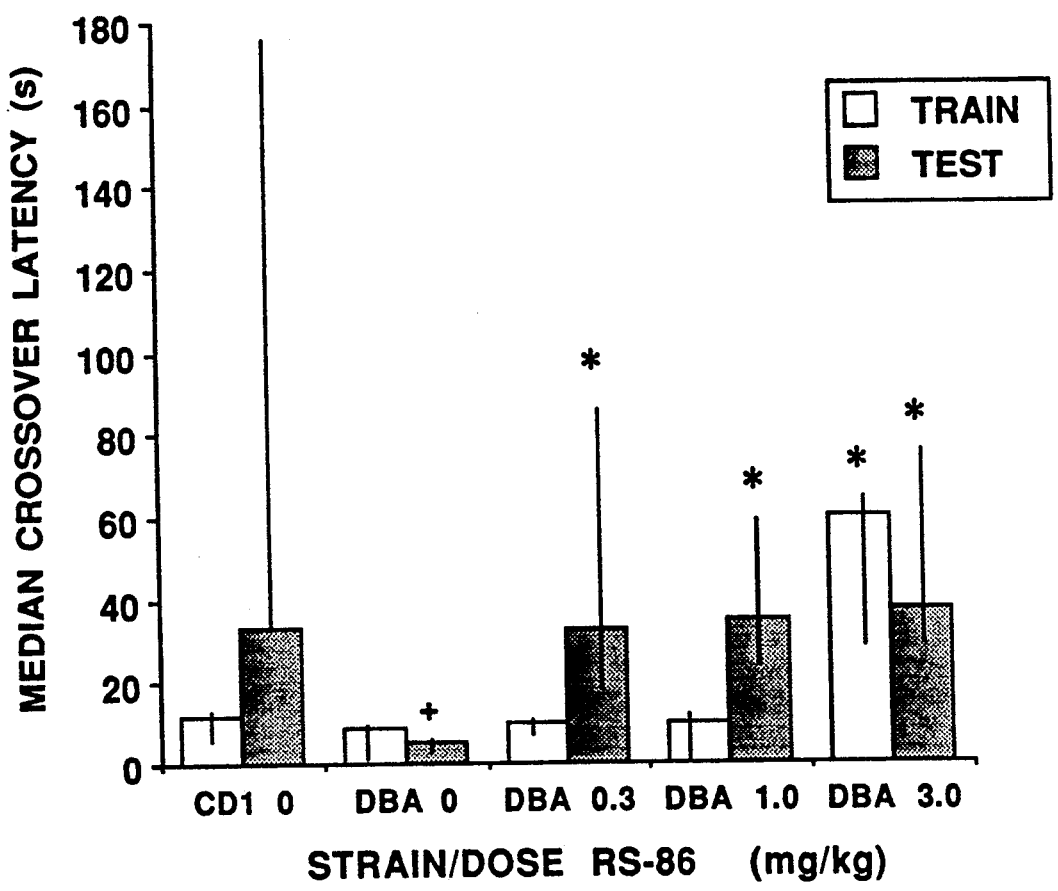
FIG. 3 is a graphical representation (bar graph) of the effects of the compound of RS-86 on the performance of CD1 and DBA mice in inhibitory avoidance studies expressed as median crossover latency time.
Figure 4:
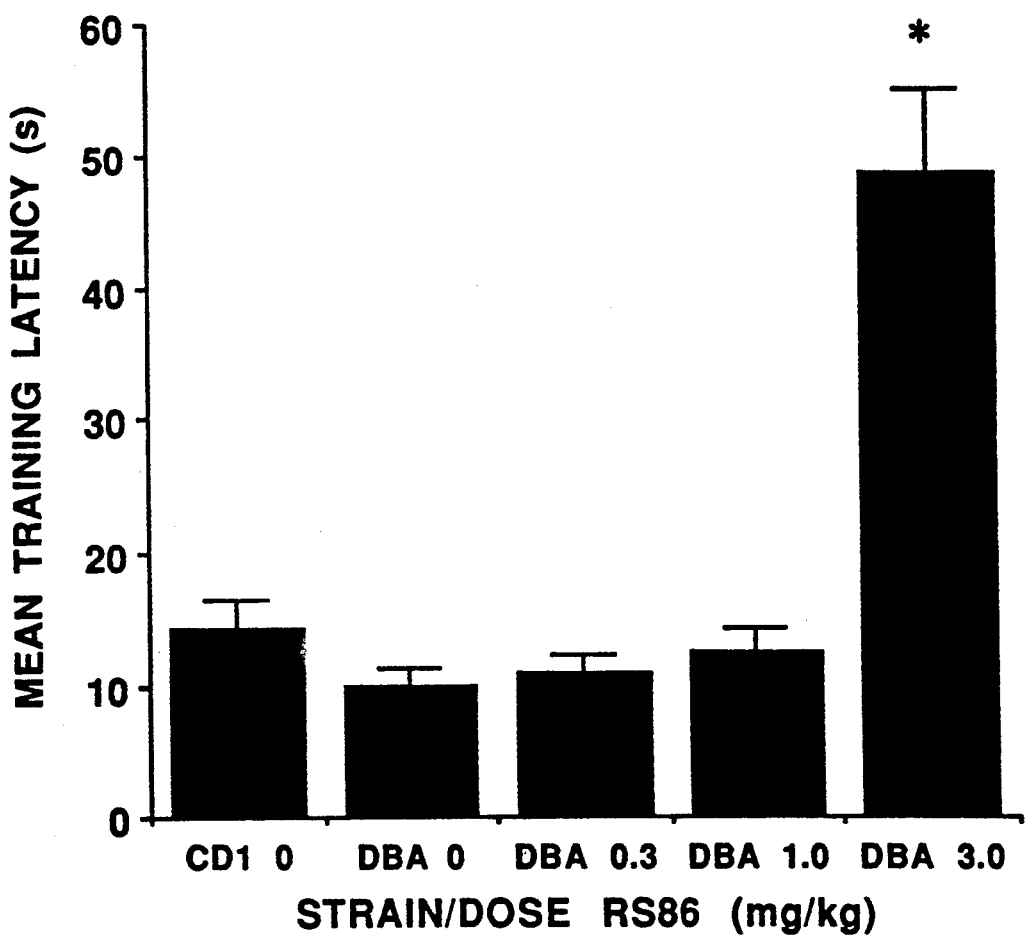
FIG. 4 is a graphical representation (bar graph) of the effects of RS-86 on training latencies measured for CD1 and DBA mice in the inhibitory avoidance studies as a function of RS-86 dose.

FIGS. 3 and 4 demonstrate that as with the compound of Example 1, RS-86 apparently eliminated the 72 hour retention deficit observed in untreated DBAs. However, the training latencies of animals dosed with RS-86 @3.0 mg/kg were significantly [$F_{(4,72)}=25.8$, $p<0.00001$] elevated relative to all other groups. Specifically, nine animals trained with this dose of RS86 completely failed to cross to the dark compartment. FIG. 4 in particular, portraying only training latencies, underscores this undesirable effect of RS-86.

B. Mouse Plus (Water) Maze Studies

The mouse plus maze probes spatial learning processes (Decker and McGaugh, *Brain Res*, 1989, 477:29). Animals are placed at the terminus of one arm of a four-arm maze submerged in opaque (powdered milk) 25° C. water. Their task is to locate a stationary escape platform hidden at the end of one arm of the maze. The platform remains in the same position across all 4 days of testing. Six daily trials are conducted, during which choice accuracy (correct or incorrect) and latency to escape (maximum=60 seconds) are recorded. Animals failing to escape within 60 seconds are gently guided to the platform, where they are allowed to sit for 20 seconds.

Previous studies demonstrated that DBA mice show a learning impairment in this task relative to C57BL/6 mice. Accordingly, adult male DBA and C57 mice (n=~10/group) were treated with the compound of Example 1 or RS-86 (0, 0.3, or 1.0 mg/kg, i.p.) approximately 45 minutes prior to 4 consecutive daily water maze sessions. Choice accuracy was assessed daily, with day 4 accuracy serving as the primary measure of learning.

Figure 5:
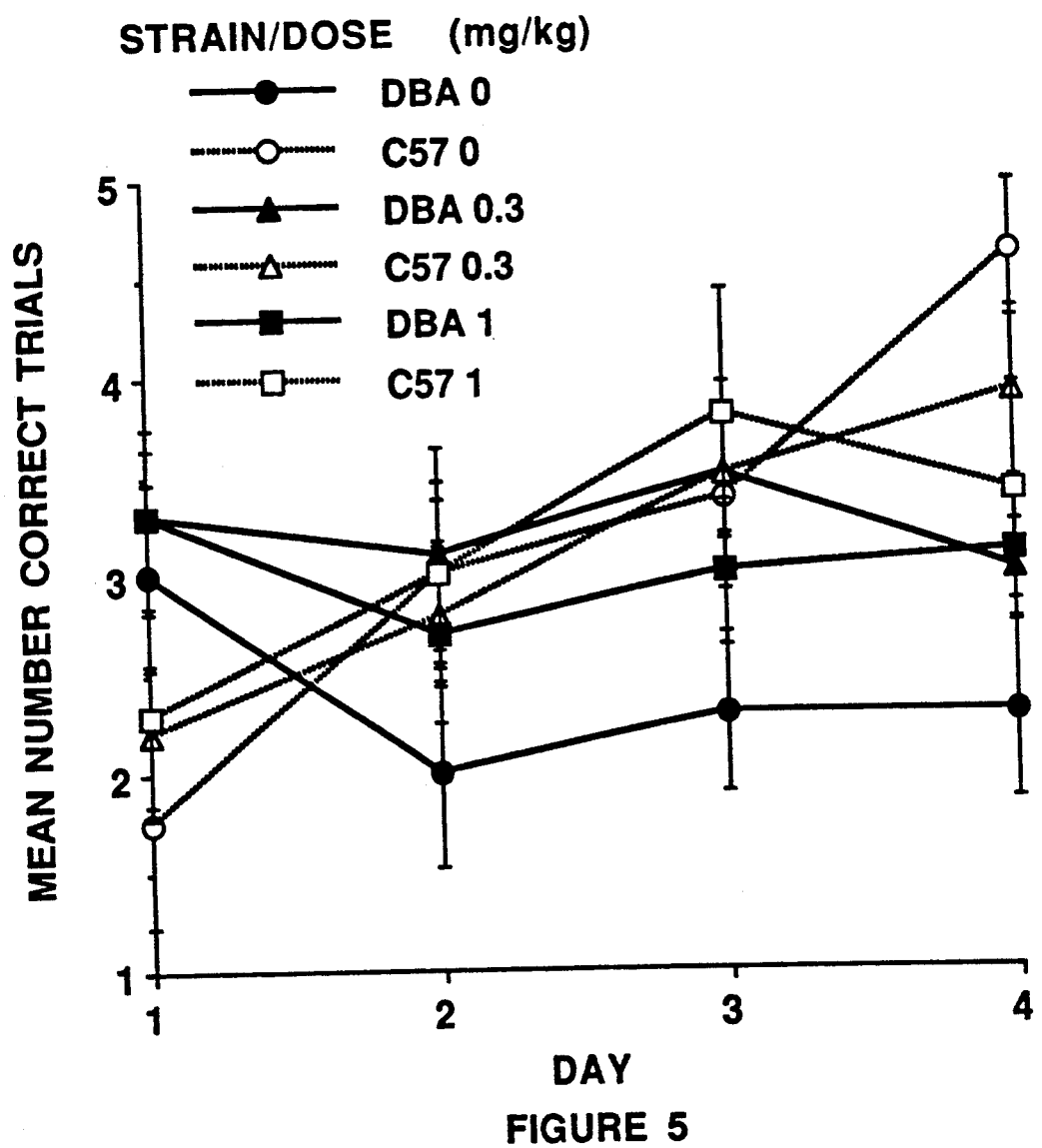
FIG. 5 is a graphical representation of the effects of various doses of the compound of Example 1 on the performance of DBA and C57BL/6 mice in the Mouse Plus Maze Study over the 4 day test period.
Figure 6:
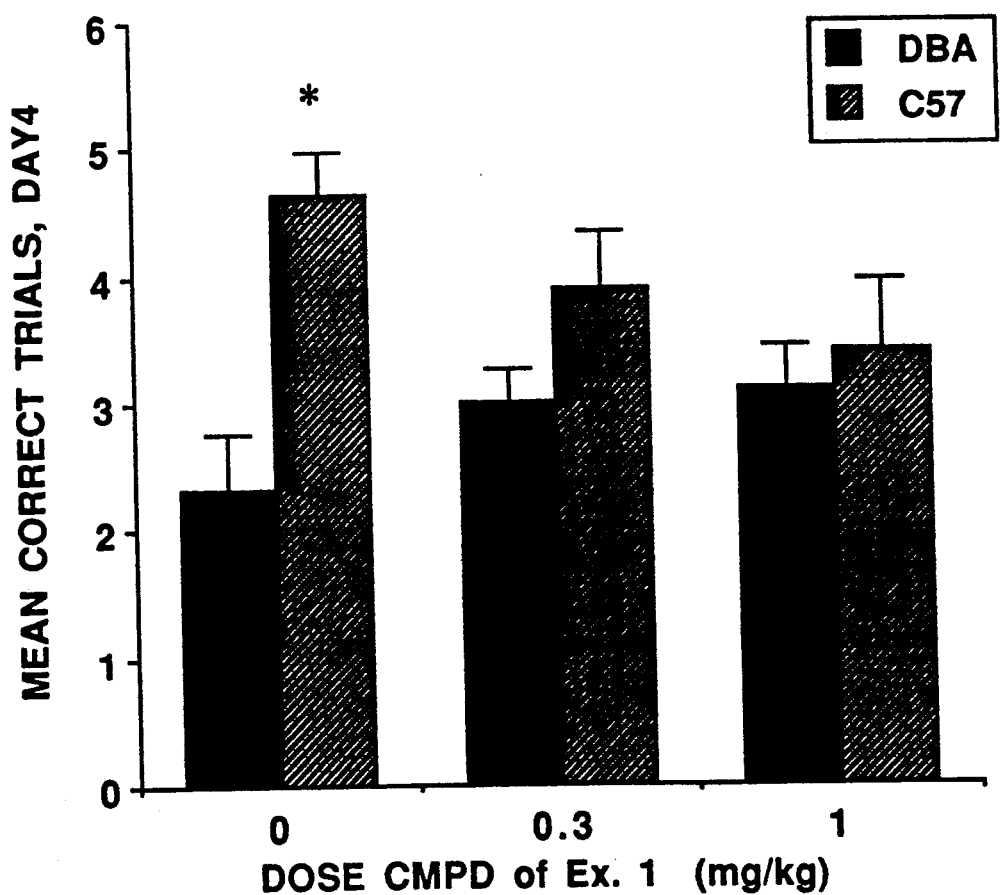
FIG. 6 is a graphical representation (bar graph) of the effects of the compound of Example 1 on the performance of DBA and C57BL/6 mice in the Mouse Plus Maze study on day 4, as a function of dose.

FIGS. 5 and 6 show the effects of the compound of Example 1 in this task. Supportive of the above studies, untreated DBA mice were significantly [$F_{(5,57)}=31.34$, $p<0.00001$] impaired relative to untreated C57 animals. Treatment with the compound of Example 1 produced a modest, albeit statistically non-significant, enhancement of learning. Overall statistical significance notwithstanding, if one argues that two correct responses represent chance performance, then DBA mice treated with 0.3 or 1.0 mg/kg of the compound of Example 1 consistently performed above chance levels beginning on the second day of testing.

Figure 7:
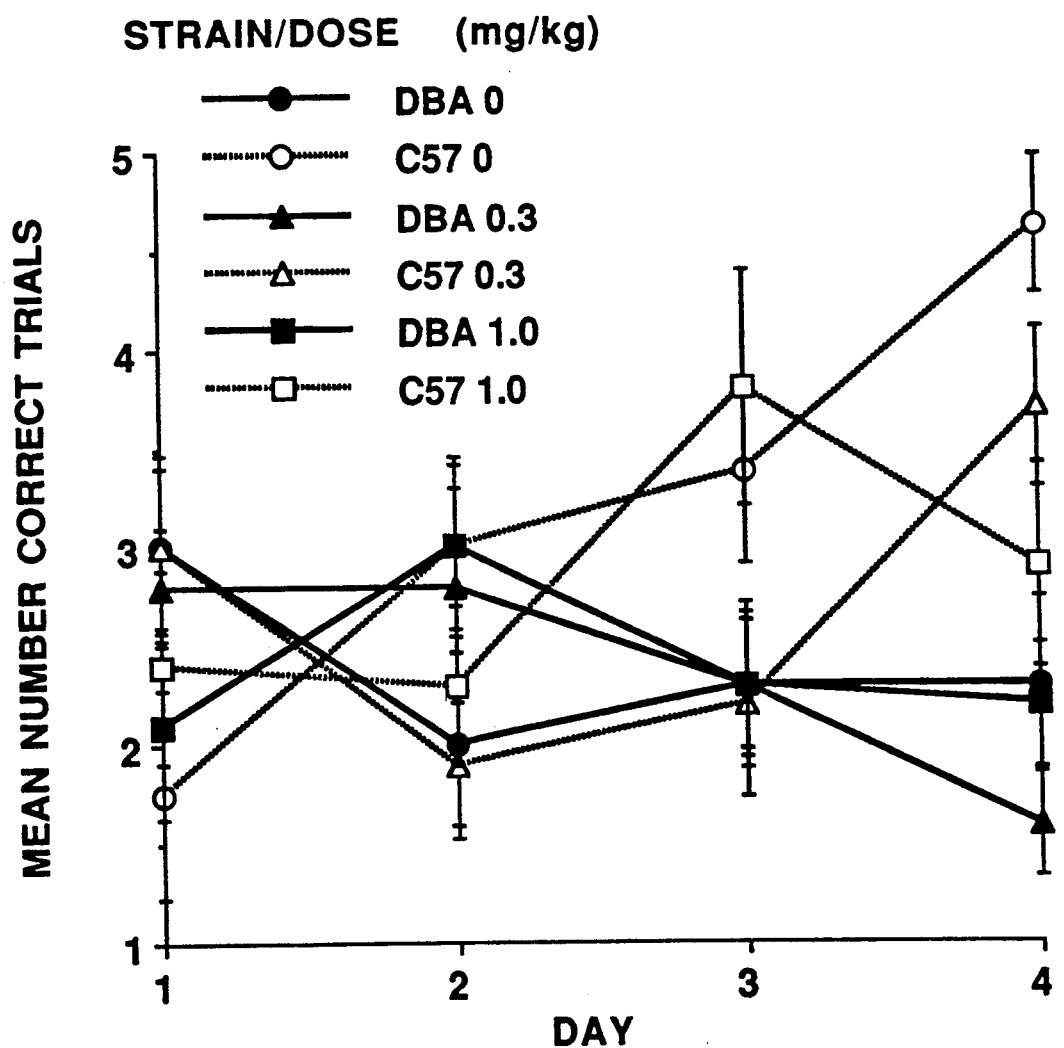
FIG. 7 is a graphical representation of the effects of various doses of RS-86 on the performance of DBA and C57BL/6 mice in the Mouse Plus Maze study over the 4 day test period.
Figure 8:
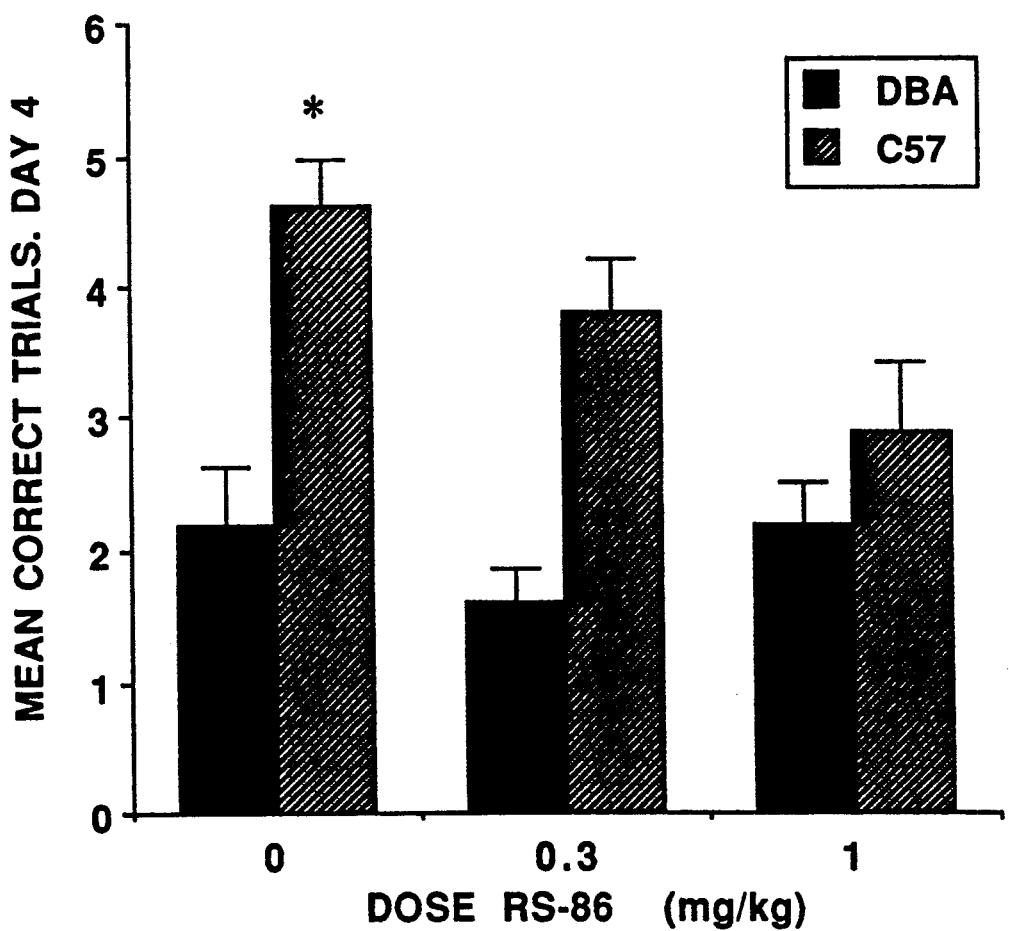
FIG. 8 is a graphical representation (bar graph) of the effects RS-86 on the performance of DBA and C57BL/6 mice in the Mouse Plus Maze Study on day 4, as a function of RS-86 dose.

In contrast (FIGS. 7 & 8), RS-86 treatment had no beneficial effect on water maze performance in either DBA or C57 mice.

In Vivo Side-Effect Profile

Undesirable side-effects such as hypoactivity and acute toxicity were also assessed.

A. Locomotor Activity Studies

Adult male CD1 mice (n=8/group) were injected with the compound of Example 1 or RS-86 (0, 0.3, 1.0, or 3.0 mg/kg, i.p.) approximately 45 minutes prior to placement in automated activity monitors (Omnitech; Columbus, Ohio). These enclosures, measuring 40×40×42 cm, are equipped with a series of photocells and generate measurements of a variety of locomotor activities.

Mean horizontal activity counts were equivalent across all doses of the compound of Example 1 (FIG. 1). Animals treated with RS-86 @3.0 mg/kg, on the other hand, exhibited a profound and significant [$F (3,28)=29.17$, $p<0.00001$] reduction in horizontal activity. Activity measurements of animals treated with 0.3 or 1.0 mg/kg RS-86 did not significantly differ from animals dosed with the compound of Example 1.

Thus, the compound of example 1 has a more favorable separation of hypoactivity from the desired activity of cognitive enhancement than does RS-86.

B. Toxicology

Doses of 0.3 and 1.0 mg/kg (i.p.) of the compound of Example 1 or RS-86 were well tolerated by male CD1 mice. At 3.0 mg/kg, the compound of Example 1 produced some dyspnea and a mild decrease in spontaneous activity. In contrast, 3.0 mg/kg RS-86 produced, in addition to dyspnea and decreased activity, classic signs of cholinostimulation: salivation, lacrimation, urination, defecation, and tremor. RS-86 3.0 mg/kg also produced a greater hypothermic response than did a similar dose of the compound of Example 1. No fatalities accrued to either drug at any of these three tested doses.

In general, the compound of Example 1 produced more benign side-effects than did RS-86.

BIOLOGICAL ACTIVITY OF EXAMPLES 3 AND 4

In Vitro Determination of Nicotinic Receptor Binding Potency

Initial screening indicated that the spirohydantoins were ineffective at interacting with muscarinic receptors and were therefore examined for activity related to the neuronal nicotinic cholinergic receptor.

Binding of [$^3$H]methylcarbamylcholine ([$^3$H]-MCC) to nicotinic receptors is accomplished using crude synaptic membranes prepared from whole rat brain (Snyder and Enna, Brain Res. 1975, 100:81). Washed membranes are stored at −80° C. prior to use. Frozen aliquots are slowly thawed and resuspended in 20 volumes of buffer (containing: 120 mM NaCl, 5 mM KCl, 2 mM MgCl$_2$, 2 mM CaCl$_2$, and 50 mM Tris-Cl, pH 7.4 @4° C.). After centrifuging at 20K×9 for 15 minutes, the pellets are resuspended in 30 volumes of buffer. Homogenate (125-150 mg protein) is added to triplicate tubes containing concentrations of test compound and [$^3$H]-MCC (3 nM) in a final volume of 500 mL. Samples are incubated for 60 minutes at 4° C., then rapidly filtered through Whatman GF/B filters presoaked in 0.5% polyethylimine using 3×4 ml of ice-cold buffer. The filters are counted in 4 mL of Ecolume (ICN). Nonspecific binding is determined in the presence of 10 mM (−)nicotine and values were expressed as a percentage of total binding. IC$_{50}$ values are determined with the ALLFIT curve-fitting program and IC$_{50}$ values are converted to Ki values using the Cheng and Prusoff correction, (Ki=IC$_{50}$/(1+[ligand]/Kd ligand). Alternatively, data are expressed as a percentage of the total specific binding.

TABLE 3

| Compound | M1 Ki(mM) | M2 Ki(mM) | Nic* Ki(mM) | Nic % Enhancement & Conc. (mM) @ Max. Effect |
|---|---|---|---|---|
| EXAMPLE 3 | >100 | >100 | >100 | +42%; 0.0001 |
| EXAMPLE 4 | 28 | >100 | >100 | +33%; 0.0001 |

*Binding to the nicotinic receptor

These data suggest that the spirohydantion compounds of Examples 3 and 4 have little affinity to directly compete for muscarinic (M1 or M2) and nicotinic neuronal binding sites. However, they do potently enhance the binding of other nicotinic ligands to the neuronal nicotinic receptor, a property consistent with putative positive allosteric modulators such as (+)2-methylpiperidine.

In Vivo Determination of Nicotinic Modulatory Action Affecting Basal Forebrain Neurotransmission Previous studies suggest that activation of neurons arising from the basal forebrain to the cerebral cortex will elicit an increase in cortical cerebral blood flow (CBF) by a mechanism that is mediated by a nicotinic receptor (refer to Background of the Invention).

General Surgery for CBF Measurement—Methods for surgical preparation of rats for electrical stimulation of brain and measurement of rCBF have been previously described (Nakai et al., Am. J. Physiol. 1982, 243:226) and are summarized below.

Studies are conducted on male Sprague-Dawley rats that are maintained in a thermally controlled (26°–27° C.) light-cycled (07.00 hour on–019.00 hour off) environment, fed standard rat chow and given water ad libitum. Anesthesia is induced with halothane (3.5%; balance O$_2$) delivered through a nose mask and maintained at 2% during the initial surgery. Thin-wall vinyl catheters (o.d.=0.03 inch) are placed in each femoral artery and vein, and the trachea is cannulated.

Animals are subsequently co-anesthetized with urethane (1.5 g/kg, s.c.) and placed in a stereotaxic frame with the head positioned so that the floor of the IVth ventricle was horizontal (incisor bar position: −11 mm.). After connecting the tracheal cannula to a small-animal respirator, the animals are paralyzed with d-tubocurarine (0.6 mg/kg/h, i.m.), and ventilated (80 cpm) with 100% O$_2$. Arterial pressure (AP) and heart rate (HR) are continuously monitored through one of the arterial catheters connected to a Statham P23Db transducer that is coupled to a chart recorder. The level of anesthesia during surgery or subsequent experimental testing is assessed by the AP response to tail pinch, with increasing levels of arousal giving rise to irregular AP readings. Booster doses of urethane (250 mg/kg, s.c.) are given as needed.

Bilateral craniotomies (approximately 4 mm×11 mm) are performed overlying the frontoparietal cortices taking care to leave the dura intact. Halothane is delivered at a reduced rate of 1% during cranial surgery and discontinued afterward. A small volume (about 0.2 ml) of arterial blood is sampled after completion of all surgery for measurement of PO$_2$, PCO$_2$ and pH by a blood gas analyzer. Arterial blood gases are maintained so that PO$_2$ was greater than 100 mm Hg, PCO$_2$=33–38 mm Hg, and pH=7.35–7.45. Maintaining these values is accomplished by adjusting the stroke volume of the ventilator. Once appropriate physiological parameters are obtained (approximately 30 min), the experimental protocol is initiated.

Electrical Stimulation of the Basal Forebrain (BF)—The BF is stimulated with cathodal current delivered through a stainless steel concentric bipolar electrode (250 mm diameter) made by Rhodes Medical Instruments (Model SNEX-100). Electrical pulses are generated by a square wave stimulator (Grass, Model S-88) and constant current is passed through a photoelectric stimulus-isolation unit (Grass, Model PSIU6). The stimulus current is measured on an oscilloscope by continuously displaying the voltage drop across a 10-ohm resistor.

The procedure for eliciting an increased cortical CBF response requires the stereotaxic placement of the stimulating electrode into the BF. For positioning, the electrode is inclined posteriorly to 18 degrees, and the stereotaxic coordinates used were 5.0 mm posterior to, and 2.6 mm lateral to bregma (stereotaxic zero reference point). Cerebrovascular responsiveness, as measured by LDF, is used to localize the most active site of the BF by stimulating with 10 second trains of 2 msec duration pulses, at a frequency of 50 Hz and intensity of 100, uA. These parameters have been shown previously to elicit maximal increases in cortical CBF (Arneric, Excerpta Medica International Congress Series, Vol. 869:381, 1989). The region of the BF that selectively affects cortical CBF is restricted, with electrode movements of 0.5 mm dorsal or ventral to this site eliciting potent vasodepressor responses in addition to the increases in CBF. Thus, the vasodepressor responses are also used to help signal the approachment of the most active BF site. When CBF increases of approximately 100% or greater are repeatedly obtained in the absence of significant changes in AP ($<10$ mm Hg) or HR ($<10$ beats/min.), and when the perfusion rate is stable in the absence of BF stimulation, the experimental testing is started.

CBF Measurement with Laser—Dopler Flowmetry (LDF)—The principles and technical aspects of LDF are presented in detail elsewhere (Bonner et al., *Appl. Opt.* 1981, 20:2097; Stern et al., *Am. J. Physiol.* 1977, 232:H441). In brief, LDF is used to assess second-to-second changes in microvascular perfusion within a restricted region (1 cubic mm) immediately beneath the laser-doppler probe placed on dura. To monitor cortical CBF, an LDF probe (0.8 mm dia.) is attached to a micromanipulator and positioned over the exposed frontal CX. The probe is positioned to avoid major surface vessels and to touch the dura without significant surface indentation or occlusion of vessels. Careful exposure and manipulation of the frontal CX in this manner does not impair cerebrovascular reactivity (Arneric et al., Brain Res. 411:212, 1987). Responses to BF stimulations were assessed within a restricted cortical region (1.3-1.8 mm anterior to, and 3.2-3.9 mm lateral to bregma), defined as frontal CX, in order to select the coordinates giving the largest enhancement of cortical perfusion. The LDF monitor (BPM 403A, TSI Inc.) displays and records blood flow readings in absolute blood flow units (ml/min/100 g). However, for the experiments discussed, these values were treated as arbitrary numbers and used only to determine relative changes in blood flow.

Intravenous (iv) administration of the compound of Example 3 (0.01-10.0 mg/kg) was examined for its effect on mean arterial pressure (MAP), resting CBF and increases in cortical CBF elicited by electrically stimulating the BF (@12.5 Hz; 100 uA; 10 second train). Consistent with the binding experiments, low concentrations were effective in enhancing resting CBF and the BF-elicited CBF response (Table 4). No remarkable effects on MAP were observed.

TABLE 4

| | % Change from Pre-Drug CONTROL | | |
|---|---|---|---|
| | MAP | Resting CBF | BF-Elicited CBF Response |
| EXAMPLE 3 (0.01 mg/kg, iv) | +5 | +23 | +39 |

Values are the mean of three experiments.

These data indicate that low concentrations of the compound of Example 3 effectively act a putative positive allosteric modulator of the neuronal nicotinic cholinergic receptor, since both ongoing discharge to affect resting cerebral blood flow, as well as the basal forebrain-elicited cerebral blood flow response, were enhanced. Moreover, the compound of Example 3 has the advantage of having no overt effects on blood pressure, unlike what is typically obtained by many other direct acting nicotinic or muscarinic agonists.

The compounds of the present invention can be used in the form of salts derived from inorganic or organic acids. These salts include but are not limited to the following: acetate, adipate, alginate, ascorbate, aspartate, benzoate, benzenesulfonate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, fumarate, hydrochloride, hydrobromide, hydroiodide, 2-hydroxy-ethanesulfonate, lactobionate, lactate, laurate, lauryl sulfate, maleate, methanesulfonate, nicotinate, 2-naphthalenesulfonate, oleate, oxalate, pamoate, palmitate, pectinate, persulfate, 3-phenylpropionate, phosphate, picrate, pivalate, propionate, stearate, succinate, sulfate, tartrate, thiocyanate, toluenesulfonate, undecanoate valerate salts and the like. Also, the basic nitrogen-containing groups can be quaternized with such agents as loweralkyl halides, such as methyl, ethyl, propyl, and butyl chlorides, bromides, and iodides; dialkly sulfates like dimethyl, diethyl, dibutyl, and diamyl sulfates, long chain halides such as decyl, lauryl, myristyl and stearyl chlorides, bromides and iodides, aralkyl halides like benzyl and phenylethyl bromides, and others. Water- or oil-soluble or dispersible products are thereby obtained.

The pharmaceutically acceptable salts of the present invention can be synthesized from the compounds of formula (I) by conventional chemical methods. Generally, the salts are prepared by reacting the free amine with stoichiometric amounts or with an excess of the desired salt forming inorganic or organic acid in a suitable solvent or various combinations of solvents.

The present invention includes one or more of the compounds of Formula (I) formulated into compositions together with one or more non-toxic pharmaceutically acceptable carriers, adjuvants or vehicles, which are collectively referred to herein as carriers, for parenteral injection, for oral administration in solid or liquid form, for rectal administration, and the like.

In order to reduce unwanted peripherally mediated side-effects, it is advantageous, to incorporate into the composition a peripherally acting anti-cholinergic or anti-muscarinic agent such as N-methylscopolamine, N-methylatropine, propantheline, methantheline, or glycopyrrolate.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particule size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycos, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used as polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, caster oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa cutter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservative, buffers or propellants as may be required. Ophthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposones can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p 33 et seq.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to 100 mg/kg body weight daily and preferably 0.01 to 10 mg/kg/day. Dosage unit compositions may contain such amounts of submultiples thereof to make up the daily dose. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

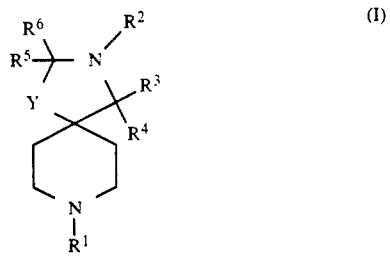

(I)

wherein
R$^1$ is hydrogen or methyl;
Y is O or

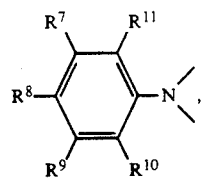

wherein R$^7$, R$^8$, R$^9$, R$^{10}$ and R$^{11}$ are independently selected from the group consisting of
(i) hydrogen
(ii) halogen,
(iii) methyl,
(iv) halomethyl,
(v) methoxy and
(vi) ethoxy, or
R$^7$ and R$^8$ or R$^8$ and R$^9$ or R$^9$ and R$^{10}$ or R$^7$ and R$^{11}$ taken together are methylenedioxy;
R$^2$ is hydrogen or methyl, R$^3$ and R$^4$ taken together form =O, and R$^5$ and R$^6$ taken together form =O or =S when Y is

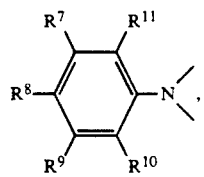

wherein R$^7$, R$^8$, R$^9$, R$^{10}$ and R$^{11}$ are as defined above, or R$^2$ is

wherein Z is O or S, R$^3$ and R$^4$ are both hydrogen, R$^5$ is methyl and R$^6$ is hydrogen when Y is O;
subject to the proviso that R$^1$, R$^2$, R$^7$, R$^8$, R$^9$, R$^{10}$ and R$^{11}$ are not all hydrogen at the same time,
or a pharmaceutically-acceptable salt thereof.

2. A compound of claim 1, wherein Y is O, R$^2$ is

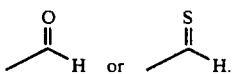

3. A compound of claim 1, wherein Y is

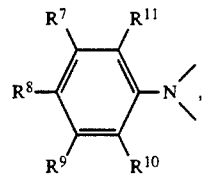

R$^3$ and R$^4$ taken together form =O, R$^5$ and R$^6$ taken together form =O or =S, and R$^7$, R$^8$, R$^9$, R$^{10}$ and R$^{11}$ are as defined in claim 1.

4. A pharmaceutical composition for treating a CNS disorder caused by a malfunction of the cholinergic system comprising a pharmaceutically-acceptable carrier and a therapeutically-effective amount of a compound of claim 1.

5. A method for enhancing cortical cholinergic neurotransmission comprising administering to a host in need of such treatment a therapeutically-effective amount of a compound of claim 1.

6. A method for treating dementia, tardive dyskinesia, hyperkinesia, mania or acute confusion disorders comprising administering to a host in need of such treatment a therapeutically-effective amount of a compound of claim 1.

7. A method for treating dementia, tardive dyskinesia, hyperkinesia, mania or acute confusion disorders comprising administering to a host in need of such treatment a therapeutically-effective amount of a compound of claim 1 in combination with a therapeutically-effective amount of a peripheral cholinergic antagonist.

8. A method for treating dementia comprising administering to a host in need of such treatment a therapeutically-effective amount of a compound of claim 1.

9. A method for treating Alzheimer's Disease comprising administering to a host in need of such treatment a therapeutically-effective amount of a compound of claim 1.

* * * * *